United States Patent [19]

Lynch

[11] Patent Number: 4,746,506
[45] Date of Patent: May 24, 1988

[54] ORGANIC NITRATE DRUG MIXTURES RESISTANT TO DETONATION BY FIRE

[75] Inventor: Matthew J. Lynch, Wilmington, Del.

[73] Assignee: ICI Americas Inc., Wilmington, Del.

[21] Appl. No.: 600,557

[22] Filed: Apr. 17, 1984

Related U.S. Application Data

[63] Continuation of Ser. No. 428,378, Sep. 29, 1982, abandoned.

[51] Int. Cl.$^4$ ...................... A61K 31/21; A61N 33/48
[52] U.S. Cl. ......................................... 424/2; 514/509
[58] Field of Search ........................... 424/2, 298, 349; 149/101, 103, 104; 514/509

[56] References Cited

U.S. PATENT DOCUMENTS

| | | | |
|---|---|---|---|
| 307,988 | 11/1884 | Robertson | 149/101 |
| 525,188 | 8/1894 | Callahan et al. | 149/101 |
| 1,905,289 | 8/1929 | Holmes | 149/104 |
| 2,140,447 | 12/1938 | Ayers | 149/101 |
| 2,140,897 | 12/1938 | Challenor et al. | 149/101 |
| 2,351,468 | 6/1944 | Woodbury | 149/101 |

FOREIGN PATENT DOCUMENTS 3954  10/1978  United Kingdom ................ 149/101

OTHER PUBLICATIONS

Lachman et al., The Theory and Practice of Industrial Pharmacy 2nd Ed., Lea & Febiger 1976 pp. 333, 341.
Foye "Principles of Medicinal Chemistry" Lea & Febiger pp. 390–394.

*Primary Examiner*—Allen J. Robinson

[57] ABSTRACT

Detonatable organic nitrates which are blended with excipients in drug mixtures for use as vasodialators such as nitroglycerine/lactose are rendered nondetonatable when burned in smoldering fires by the incorporation therewith of minor amounts of alkaline solid material such as magnesium carbonate and hydroxide.

1 Claim, No Drawings

4,746,506

ORGANIC NITRATE DRUG MIXTURES RESISTANT TO DETONATION BY FIRE

This is a continuation of application Ser. No. 428,378 filed Sept. 29, 1982, now abandoned.

This invention is directed to drug mixtures containing high concentrations of organic nitrate compounds such as nitroglycerin dispersed in an inert excipient and a minor amount of an alkaline solid which acts as a detonation desensitizer when the mixture is burned under oxygen deficient conditions. The nitrate mixtures which include isosorbide dinitrate mannitol hexanitrate and pentaerthytol tetranitrate (PETN) are used in preparing tablets in more dilute concentrations which are used as vasodilating drugs especially in the treatment of angina. Alkaline solid desensitizers may be selected from alkali and alkaline earth metal carbonates, bicarbonates, hydroxides, hydrous oxides, and include such materials as ammonium carbonate.

Detonatable organic nitrates in concentrations ranging from 5-50% by weight such as nitroglycerin, isosorbide dinitrate and PETN have been dispersed in organic excipients such as lactose, starch, mannitol, sorbitol, sugar and polyvinylpyrrolidone and inorganic materials such as bentonite, attipulgite and silica. Such materials are thereafter diluted further when tablets are made for medicinal use. Blends of concentrated organic nitrates are generally considered stable and do not detonate even when submitted to high energy shock waves such as that supplied by a number 8 blasting cap. Furthermore, concentrated organic nitrate/excipient blends have been considered safe and have been burned under oxygen rich conditions without incident. Waste materials containing the nitrate have been disposed of by burning for some time without incident. Recently however, it was discovered that a commercially available drug mixture containing 10% nitroglycerine and 90% lactose could be detonated when burned in oxygen deficient, scorching and smoldering fires.

It is the object of this invention, therefore, to provide an organic drug mixture resistant to detonation in smoldering fires which comprise, 5-50% by weight of an organic nitrate selected from nitroglycerin, isosorbide dinitrate mannitol hexanitrate and pentaerythitol tetranitrate, an inert nonalkaline excipient and an effective amount of a desensitizer solid alkaline material selected from alkali and alkaline earth metal carbonates, bicarbonates, hydroxides, hydrous oxides and other salts such as the ammonium salts.

The compositions of the invention can be made by simple blending techniques well known to the art for handling explosive materials. For example, the nitrate can be added to a mixture of excipient containing the desensitizer, the desensitizer can be added to a blend of nitrate plus excipient or alternatively all three may be combined at once. The choice of blending method may require a different concentrations of desensitizer to gain equivalent results. In a preferred procedure the desensitizer is added to a blend of the nitrate in excipient so that the nitrate particle is coated with the desensitizer solid material.

The organic nitrate/excipient blend can be made by first dissolving the nitrate in a highly volatile solvent such as alcohol, acetone or the like and thereafter adding the nitrate solution to a commercial blender containing either the inert excipient or a blend of the excipient with the desensitizer. One suitable procedure involves adding an acetone solution of nitrate such as nitroglycerin to an evacuated rotating v-shaped blender such as that made by the Patterson-Kelly Corporation. The solvent containing nitrate distributes over the surface of the solid powdered excipient after which the solvent evaporates leaving a fully blended nitrate coated solid. A minor amount of the powdered desensitizer may be coated over the nitrate containing particle in the same blending device. It is further contemplated that the ingredients can be blended in an aqueous paste solution after which it may be extruded and dried by conventional techniques. Many other commercially available blending devices normally acceptable for use with explosives may be employed for making the mixture.

The drug mixtures usually will contain from 5-50% by weight of the organic nitrate dispersed in an inert non-alkaline solid excipient and a minor amount of alkaline solid material as a desensitizer. Excipient blends of nitroglycerine can be stabilized against detonation when they contain at least about 0.05 parts of alkaline desensitizer per each part of organic nitrate. In most instances the larger amounts of desensitizer in the blend offer little improvement up to 0.2 parts per part organic nitrate and higher up to equal amounts.

Desensitizing alkaline solid materials may be selected from the carbonates, bicarbonates, hydroxides and hydrous oxides of alkali and alkaline earth metals selected from lithium, sodium, potassium, calcium, magnesium and barium. Ammonium carbonate is effective at higher concentration, however, a darkened product results after standing. When lactose is used as an excipient, magnesium hydroxide and carbonate are preferred since they have less tendency to darken the blend.

It is contemplated that any inert organic non-alkaline organic or inorganic excipient can be employed. Commonly used are such materials as lactose, starch, sugar, flour, mannitol, sorbitol and polyvinylpyrrolidone. Inorganic materials may be selected from clay such as bentonite and attipulgite, silica and the like.

In addition to these essential ingredients coloring agents, flavors or additional medications may be employed.

The following examples are presented to demonstrate the effectiveness of various alkaline solid materials in stabilizing nitroglycerin/lactose blends. However, the equivalent results are expected to be obtained with compositions containing mannitol hexanitrate, isosorbide dinitrate, and PETN in concentrations ranging from 5 to 50% by weight. In the following examples all proportions are expressed in parts by weight unless otherwise expressed.

Preparation A 10 parts of nitroglycerin dissolved in 90 parts acetone held in a polyethylene tank is added to 90 parts hydrous lactose USP held in a commercially available rotating ribbon type blender turning at low speed. When all the acetone solution has been added usually over a period of about 5 hours and thoroughly mixed in the ribbon blender the material is transferred to paper covered trays held on a drying cart and placed in a drying room for at least 16 hours at about 50° C. The material is then passed through a #10 U.S. Sieve Series screen and stored in polyethylene lined fiber drums.

EXAMPLES

Varying amounts of Preparation A were placed in a ribbon blender and combined with a pulverized alkaline solid desensitizer to form evenly distributed blends containing 0.05, 0.1 and 0.2 parts of desensitizer per part nitroglycerine wherein the ratio of lactose to nitroglycerine was 9:1.

Burn tests were conducted for each of the densensitized blends by placing 2 pounds of nitrate mixture in a 3-mil thick polyethylene bag measuring 6 inches in diameter and 12 inches in length. The open end was tied off to form a chub measuring 6 inches in diameter by 10 inches in length. These samples were then placed in a 3 AF cap carton and taped. 5 samples of each blend including the control was prepared this way for burn testing.

Each sample was burned at an outdoor test ground as follows:

1 multiwall paperbag (23"×35") having 3 paper layers and 1 polyethylene layer was placed on the bottom of a hole dug in the ground measuring 2½ feet square and 6 inches deep. In the center of the bag over a 16×16 inch area were placed 5 layers of pine wood furring strips measuring ¾ inch×2⅝ inch×16 inches. 4 strips were spaced 4 inches apart parallel to one another on the bag as a first layer. The second layer was placed on top of the furring strips at 90° angle thereto spaced 4 inches apart. 3 more layers were piled in alternating directions to form the 5 layers of furring strips. 2 quarts of No. 2 fuel oil was then poured over the wood strips. The 2 pound sample was then placed on top of the pile of wood. The fire was ignited and watched from behind a barricade. The wind velocity was no greater than 10 miles per hour. After about 37 to 42 minutes the blend containing no desensitizer had detonated. Test results for the various desensitizer materials tried appear in Table 1.

While concentrations of desensitizer ranging to as low as 0.05 parts per part nitrate was found to be effective, it is contemplated that even lower quantities may be employed if the alkaline solid is added wet to the ribbon mixer after the nitroglycerin solvent combination is blended with the lactose, since the desensitizer can be more evenly coated over the lactose/nitrate particle.

While other nitrates such as isosorbide dinitrate, PETN, and mannitol hexanitrate are somewhat less sensitive than nitroglycerine it is expected that the incorporation of the desensitizer materials will be effective in reducing the detonation hazard if similar detonating conditions arise in the blend.

TABLE 1

| Example No. | Desensitizer | Concentration (parts by wt per part nitrate) | Detonation Test Results | |
|---|---|---|---|---|
| | | | No. of Samples | No. of Detonations |
| (Control) | none | 0 | 5 | 5 (37–42 min.) |
| 1 | $NaHCO_3$ | .2 | 5 | 0 |
| 2 | $NaHCO_3$ | .05 | 5 | 0 |
| 3 | $Na_2CO_3$ | .2 | 5 | 0 |
| 4 | $MgCO_3$ | .2 | 5 | 0 |
| 5 | $MgCO_3$ | .05 | 4 | 0 |
| 6 | $Mg(OH)_2$ | .2 | 5 | 0 |
| 7 | $Mg(OH)_2$ | .05 | 4 | 0 |
| 8 | $CaCO_3$ | .2 | 5 | 0 |
| 9 | $CaCO_3$ | .05 | 4 | 0 |
| 10 | $(NH_4)_2CO_3$ | .2 | 5 | 0 |
| 11 | $(NH_4)_2CO_3$ | .1 | 4 | 4 |
| 12 | $(NH_4)_2CO_3$ | .05 | 5 | 5 |
| A | $Al(OH)_3$ | .2 | 5 | 2 |
| B | $Al(OH)_3$ | .5 | 5 | 4 |

What is claimed is:

1. A composition comprising a blend containing 1 part by weight nitroglycerine, 9 parts by weight lactose and 0.05–0.2 parts by weight of an alkaline material selected from the group consisting of magnesium hydroxide, magnesium carbonate, calcium carbonate, sodium bicarbonate, sodium hydroxide and sodium carbonate.

* * * * *